United States Patent
Bürkle

(10) Patent No.: US 6,210,893 B1
(45) Date of Patent: Apr. 3, 2001

(54) AUTOMATED QUANTIFICATION OF DNA STRAND BREAKS IN INTACT CELLS

(76) Inventor: Alexander Bürkle, Hans-Toma-Strasse 18, Leimen (DE), D-69181

( * ) Notice: Subject to any disclaimer, the term of this patent is extended or adjusted under 35 U.S.C. 154(b) by 0 days.

(21) Appl. No.: 09/297,224

(22) PCT Filed: Oct. 21, 1997

(86) PCT No.: PCT/DE97/02458

§ 371 Date: Aug. 5, 1999

§ 102(e) Date: Aug. 5, 1999

(87) PCT Pub. No.: WO98/17824

PCT Pub. Date: Apr. 30, 1998

(30) Foreign Application Priority Data

Oct. 23, 1996 (DE) ................................. 196 43 721

(51) Int. Cl.$^7$ .............................. C12Q 1/68; C12Q 1/02; C12P 19/34
(52) U.S. Cl. ................ 435/6; 435/29; 435/91.1
(58) Field of Search .................... 435/6, 29, 91, 435/501, 519, 543; 436/818; D14/100, 114.1; 364/400

(56) References Cited

U.S. PATENT DOCUMENTS 5,006,460    4/1991   Thomas Jr. et al. .

FOREIGN PATENT DOCUMENTS 3434396    3/1986   (DE) .
0628817  * 6/1993   (EP) .

OTHER PUBLICATIONS

Sano et al., "Immuno–PCR: Very sensitive antigen detection by means of specific antibody–DNA conjugates," Science, 1992, vol. 258, No. 5079, pp. 120–122.*

Birnboim and Jevcak, 1981, "Flurometric Methods for Rapid Detection of DNA Strand Breaks in Human White Blood Cells Produced by Low Doses of Radiation," *Cancer Research* 41:1889–1892.

Saravanan et al., 1993, "A modified flow injection analysis method to quantify DNA strand–breaks," *Med. Sci. Res.* 21:535–538.

Stout and Becker, 1982, "Fluorometric Quantitation of Single–Stranded DNA: A Method Applicable to the Technique of Alkaline Elution," *Analytical Biochemistry* 127 (302–307.

* cited by examiner

*Primary Examiner*—John S. Brusca
*Assistant Examiner*—Young Kim
(74) *Attorney, Agent, or Firm*—Pennie & Edmonds LLP

(57) ABSTRACT

The present invention relates to an automated method of quantifying DNA strand breaks in intact cells whereby (a) cells are lysed in order to release DNA, (b) the lysate is subjected to an alkaline denaturation process, (c) neutralization occurs, (d) a fluorescent dye is added, and (e) fluorescence is read off a fluorometer, and the method is characterized in that all pipetting stages are carried out in automated fashion by means of a pipetting device in a lightproof housing. The invention further relates to a device to carry out said method, comprising a lightproof housing, a temperature controlled base plate, a system of pipetting nozzles and a fluorometer to measure the fluorescent intensity of DNA.

15 Claims, No Drawings

AUTOMATED QUANTIFICATION OF DNA STRAND BREAKS IN INTACT CELLS

This application claims priority to the German Patent Application 1 96 43 721.0, filed on Oct. 23, 1996.

I. FIELD OF THE INVENTION

The present invention relates to an automated method of quantifying DNA strand breaks in intact cells and a device to carry out the method.

II. BACKGROUND OF THE INVENTION

The quantitative detection of DNA strand breaks is of great significance for many fields of biomedical research and diagnosis already today. The mechanisms of DNA-damage and DNA repair and their disturbances can be investigated via the detection of DNA strand breaks. Furthermore, it is thereby possible to carry out toxicological screening of substances such as chemicals, natural substances or pharmaceutical preparations. Moreover, various cell and tissue samples from patients can be examined for DNA damage and DNA repair capacity, respectively, by quantifying DNA strand breaks. This is of interest for what is called monitoring the effectiveness of radiation therapy and cytostatic chemotherapy, respectively, in the malignant cells to be killed before and during the treatment. It is also possible to evaluate the side-effect risk of radiation therapy and chemotherapy, respectively, before the therapy is started by examining normal (nonmalignant) cells as to DNA strand breaks. The examination of DNA strand breaks is also significant within the scope of preventive medicine for the screening for individuals having a high degree of DNA damage and low DNA repair capacity, respectively. A greater cancer risk has to be assumed for these persons, so that an especially close-knit preventative program is indicated for them. In this connection, what is called biomonitoring must also be considered in industrial medicine. Here, standardized DNA damage treatments would each be made with the proband's cell material to be tested.

So far, there have been some methods of examining DNA strand breaks, which are, however, very time-consuming and labor-intensive, since they must mostly be carried out manually. Another drawback of these methods is the care which must urgently be taken in the various steps so as not to reach false-positive or false-negative results. The "alkaline elution" has to be mentioned as a known method of examining DNA strand breaks. Here, a controlled, alkaline denaturation of the DNA is induced in a cell lysate. The strand break frequency is measured by determining the elution rate of the single-stranded DNA fragments through a suitable polycarbonate filter. Another known method is what is called the "comet assay". This is an in situ assay which can be carried out in various ways. In this case, cells must be embedded in an agarose gel. Following lysis "in situ" an electric field is applied, which results in a more or less marked migration of chromatin out of the nucleus. The microscopically readable migration path is considered a standard that applies to the number of DNA strand breaks. In addition, the "Fluorescence-detected Alkaline DNA Unwinding" (Birnboim, H. C. and Jevcak, J. J., 1981, Cancer Res. 41:1889–1892, abbreviated as "FADU-Assay", is also known for measuring DNA strand breaks. Here, test cells are lysed and the cellular DNA exposed in this way, which depending on the pretreatment of the cells has a more or less large number of single-strand or double-strand breaks is then subjected to denaturation under accurately controlled conditions, whereby the DNA double strand is converted into single strands. In practice, this is effected by an extremely careful piling-up of an alkaline solution, each mixture with the lower phase (the lysate) having to be avoided by all means. Within some minutes, part of the alkaline solution diffuses into the lysate. The alkaline denaturation then starts in each case from the DNA break ends and chromosome ends, respectively, and proceeds linearly, namely in both orientations in the case of a single-strand break. After stopping this alkaline DNA-unwinding by neutralization, the rest of the non-denatured DNA which remains in the sample is measured with non-denatured DNA via the intensity of the ethidium bromide fluorescence. The amount of denatured DNA calculated therefrom is a direct standard that is applied to the number of DNA strand breaks present at the time of cell lysis. The fluorescence measurement is standardized so that it applies (i) to those cell lysates (referred to as "T samples") in which no denatured pH was reached because the neutralization buffer had been added prior to the addition of the alkaline solution and (ii) to those lysates (referred to as "B samples") which had been provided with a very large number of DNA breaks by DNA shearing (e.g., by means of ultrasound treatment) prior to the alkaline denaturation. In the case of the T sample the content of denatured DNA is set to 0%, whereas the content of denatured DNA in the B sample is set to 100%. However, the FADU assay is very labor-intensive and susceptible to failure because several high-precision pipetting steps and the accurate observance of time and temperature conditions are required for each individual sample. In some steps attention has to be paid to the fact that the contents of the sample tubes comprising several piled-up liquid phases are not mixed. With regard to the required quadruple parallel determinations, the T and B samples which always have to be carried along and the large number of samples to be determined this adds up to an immense pipetting work, each pipetting step having to be carried out with the utmost constant care. In this connection, it is aggravating that the FADU assay must be carried out while the laboratory is darkened, since the cell lysates are very sensitive to light.

As explained already, the drawback of all of these methods is that they are very labor-intensive and the sample throughput per time unit is not very high. Thus, about 3 manhours are required to manually carry out the FADU assay with 30 samples. As regards the alkaline elution 16 hours 2 of them manhours) have to be estimated for about 36 samples.

In the case of the comet assay even 8 manhours are required to process only 20 samples.

Therefore, it is the object of the present invention to provide a method of quantifying DNA strand breaks, which can be carried out easily, has a good sample throughput per time unit and supplies reliable results. The object of the present invention also consists in providing a device by means of which the method can be carried out.

III. SUMMARY OF THE INVENTION

The present invention relates to an automated method of quantifying DNA strand breaks in intact cells and a device to carry out the method.

IV. DETAILED DESCRIPTION OF THE INVENTION

It is the object of the present invention to provide a method of quantifying DNA strand breaks, which can be carried out easily, has a good sample throughput per time unit and supplies reliable results. The object of the present invention also consists in providing a device by means of which the method can be carried out.

This object is achieved by a method according to claim 1. Furthermore, this object is achieved by a device according to claim 5. Advantageous embodiments follow from the dependent claims.

The inventor recognized that there was a demand for standardizing the examination of DNA strand breaks. This is achieved by the highest possible automation of the method.

The method according to the invention distinguishes itself in that (a) the cells are lysed in order to release DNA,
(b) the lysate is subjected to an alkaline denaturation process,
(c) neutralization occurs,
(d) a fluorescent dye is added, and
(e) the fluorescence is read off a fluorometer, all of the pipetting stages being carried out in automated fashion by means of a pipetting device in a lightproof housing and preferably the fluorescence measurements are also carried out in automated fashion.

The method according to the invention regarding what is called the "P" samples comprises preferably the following individual steps, the pipetting stages being carried out by means of an automatic pipetting device ("pipetting robot"):

1) placing a reaction vessel, e.g., a microtiter plate, containing adherent cells in cell culture medium or suspension cells in medium, preferably in solution B, in a darkened pipetting station
2) in the case of adherent cells: drawing off the medium; incubation temperature 0° C.; then immediately
3) in the case of adherent cells: adding solution B (0° C.); incubation temperature 0° C., then immediately
4) adding solution C (room temperature); incubation temperature 0° C.; 5–20 minutes (preferably 10 minutes)
5) adding solution D (0° C.) (must be piled up without being vortexed); incubation temperature 0° C.; then immediately
6) adding solution E (0° C.) (must be piled up without being vortexed); incubation temperature 0° C.; 15–45 minutes (preferably 30 minutes)
7) adjusting the incubation temperature to about 15° C.; 30–90 minutes (preferably 60 minutes)
8) adding solution F (0° C.); mixing; incubation temperature 0° C.; 5–15 minutes (preferably 10 minutes)
9) shearing the sample, e.g., by rapid pipetting up and down or ultrasonic treatment,
10) adding solution G (room temperature); incubation temperature about 20° C.; 5–20 minutes (preferably 10 minutes)
11) reading the fluorescence intensities
12) data evaluation.

The solutions employed are, e.g., those mentioned in Bimboim et al., 1981, Cancer Res. 41:1889–1892. In detail these are:

Solution B: 0.25 M meso—inositol—10 mM sodium phosphate—1 mM MgCl$_2$ (pH 7.2)
Solution C: 9 M urea—10 mM NaOH—2.5 mM cyclohexane diamine tetraacetate—0.1% sodium dodecylsulfate (=lysis buffer; storage at room temperature)
Solution D: 0.45 volume of solution C in 0.20 N NaOH (=alkaline solution I)
Solution E: 0.40 volume of solution C in 0.20 N NaOH (=alkaline solution II)
Solution F: 1 M glucose—14 mM 2-mercaptoethanol (=neutralization solution)
Solution G: ethidium bromide 6.7 µg/ml—13.3 mm NaOH (storage at room temperature)

The above-mentioned times, temperatures and solutions can, of course, vary within certain limits. These variations are within the skill of a person skilled in the art and can be determined by means of routine experiments.

In a preferred embodiment, solutions D and E are applied combined in one step instead of two steps (steps 5) and 6)).

In the operating cycle for samples in which the content of denatured DNA can be set to 0% (referred to as "T samples" above), step 8) directly precedes step 5) already. In the operating cycle for sample in which the content of denatured DNA can be set to 100% (referred to as "B samples" above), step 9) directly precedes step 7) already.

The percentage D of double-stranded DNA which is still found in the sample following the partial alkaline treatment is a standard that is applied to the number of strand breaks at the time of lysis and can be calculated as follows:

$$D(\%)=(P-B)./.(T-B)\times 100$$

In place of ethidium bromide which is known to be mutagenic, it is also in principle possible to use another non-toxic fluorescent dye which is intercalated in double-stranded DNA (e.g., Sybr-Green™) in solution G.

The expression "adherent cells" refers to those cells which can be cultured in a reaction vessel, e.g., on a microtiter plate, as a monolayer in cell culture medium. Suitable cell culture mediums are the purchasable media with which the person skilled in the art is familiar and which are selected depending on the cell type to be grown. Some hours to about one day later the cells grown on the reaction vessel can be placed directly in the device. Examples of adherent cells are fibroblasts, HeLa cells and most tumor cells.

However, it is also possible to use "suspension cells". Suspension cells are cells which cannot be cultured as monolayer on cell culture plates. The suspension cells must first be centrifuged off the corresponding medium and then be resuspended in a buffer, e.g., in solution B, before they can be filled in a reaction vessel, e.g., a microtiter plate, and be examined according to the above scheme. Examples of suspension cells are blood cells, such as leukocytes, or lymphoid cell lines.

In a preferred embodiment, the process according to the invention can also be extended to the quantification of certain damage of DNA bases. To this end, the cell lysate which was treated with a lysis buffer containing less urea than solution C is subjected to an incubation using a purified DNA repair endonuclease prior to the alkaline denaturatin, which recognizes DNA damage determined in a highly specific way (e.g., 8-oxaguanine and pyrimidine dimers, respectively) and cuts locally the affected DNA strands, so that now one DNA strand break forms for each damaged base. These additional breaks generated in vitro can then be determined immediately afterwards by the measuring method according to the invention. An example of such an endonuclease is what is called the "FAPY enzyme". By this, the field of application of the method according to the invention can be extended considerably, namely to the highly specific quantification of unrepaired primary damage in DNA bases.

The device according to the invention is in principle a pipetting robot which comprises a lightproof housing. The reaction vessel, preferably the microtiter plate, is placed therein on a temperature controlled base plate which can raise the temperature of the samples from 0° C. to 30° C. The device comprises a system of pipetting nozzles for withdrawing liquids from, and adding them to, respectively, the reaction vessel, preferably the microtiter plate. Another component of the device is a fluorometer having an excitation wavelength of 490–550 nm, preferably 520 nm, and an emission wavelength of 570–610 nm, preferably 590 nm. The fluorometer is equipped such that the fluorescence intensity in each well of the preferred microtiter plate can be read in parallel or sequentially "in situ". The expression "fluorometer" also comprises a simple device permitting the observation of the fluorescence phenomenon by means of a light source and two different filters. The device according to the invention also comprises preferably a microprocessor as well as a printer, and plotter, respectively.

Advantages of the method according to the invention are represented by the fact that by using the device according to the invention a microtiter plate having 96 measuring points can be treated in less than 2 device hours. In contrast thereto, the working time for the staff is only several minutes as compared to the above-mentioned periods required for the manual examination of DNA strand breaks. Moreover, the cell lysis can be made directly with adherent single-layer cell cultures by the method according to the invention. The latter is of special interest because by this the preceding removal of cells from the substrate (e.g., by trypsin) is not necessary. Thus, corresponding centrifugation steps can be omitted, which are (i) time-consuming and costly and (ii) can artificially already result in the induction of DNA breaks and unfavorably affect the DNA repair behavior of the cell, respectively. Thus, the method according to the invention offers the additional advantage of measuring the DNA damage and repair in an unadulterated form.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description. Such modifications are intended to fall within the scope of the appended claims.

V. EXAMPLE

HeLa cells are placed with DMEM medium (Dulbelcco's modified essential medium) plus 10% fetal calf serum in the wells of a microtiter plate suitable for cell culture and incubated for 12 hours, the cells growing completely. Thereafter, the intact cells are exposed to radioactive radiation ($^{60}Co\ \gamma$ radiation) at 0° C. (on ice). Then, the method according to the invention is carried out as follows:

1) placing the microtiter plate in the darkened pipetting station,
2) drawing off the medium; temperature of the base plate 0° C.; then immediately
3) adding 40 $\mu$l of solution B (0° C.); temperature of the base plate 0° C., then immediately
4) adding 40 $\mu$l of solution C (room temperature); temperature of the base plate 0° C.; incubation for 10 minutes
5) adding 20 $\mu$l of solution D (0° C.) (must be piled up without being vortexed); temperature of the base plate 0° C.; then immediately
6) adding 20 $\mu$l of solution E (0° C.) (must be piled up without being vortexed); temperature of the base plate 0° C.; 15–45 minutes (preferably 30 minutes)
7) heating the base plate to about 15° C.; 60 minute of incubation
8) adding 80 $\mu$l of solution F (0° C.); mixing; temperature of the base plate 0° C.; incubation for 10 minutes
9) shearing the sample, e.g., by rapid pipetting up and down
10) withdrawing 100 $\mu$l and transferring it to a new microtiter plate
11) adding 150 $\mu$l of solution G (room temperature); temperature of the base plate about 20° C.; incubation for 10 minutes
12) reading the fluorescence intensities by means of the installed fluorometer (excitation wavelength 520 nm; emission wavelength 590 nm)
13) data evaluation.

The compositions of solutions B to G are indicated as outlined above.

In the operating cycle for samples whose content of denatured DNA shall be set to 0% (referred to as "T samples" above) step 8) directly precedes step 5). In the operating cycle for samples whose content of denatured DNA can be set to 100% (referred to as "B samples" above) step 9) directly precedes step 7.

In order to check the reliability of the method, all values were determined four times and the difference from one another was calculated. This data evaluation resulted in the fact that the determinations yielded reliable values, the differences of the four determinations being around 2%.

All references cited within the body of the instant specification are hereby incorporated by reference in their entirety.

What is claimed:

1. A method of quantifying strand breaks in the DNA of cells, comprising:
   (a) lysing cells in order to release DNA, whereby a cell lysate is generated;
   (b) exposing said cell lysate to an alkaline denaturation process, whereby said cell lysate is neutralized;
   (c) contacting said cell lysate with a fluorescent dye; and
   (d) measuring the fluorescence from said fluorescent dye in contact with said cell lysate, using a fluorometer;
   wherein steps (a) to (d) are carried out in automated fashion utilizing a pipetting device in a lightproof housing.

2. The method of claim 1, wherein said method takes place in microtiter plates.

3. The method of claim 1, wherein said fluorescent dye intercalates in double-stranded DNA.

4. The method of claim 1, wherein said fluorescence is measured at an excitation wavelength of 520 nm and an emission wavelength of 590 nm.

5. A device to carry out the method of claim 1, wherein said device comprises a lightproof housing, a temperature controlled base plate, a system of pipetting nozzles and a fluorometer to measure the fluorescence intensity of DNA.

6. The device of claim 5, wherein said device further comprises a microprocessor.

7. The device of claim 5, wherein the temperature controlled base plate is adjustable to temperatures from 0 to 30° C.

8. The device of claim 5, wherein the fluorometer measures at an excitation wavelength of 520 nm and an emission wavelength of 590 nm.

9. The method of claim 3, wherein said fluorescent dye is ethidium bromide.

10. The device of claim 6, wherein said device further comprises a printer.

11. The device of claim 6, wherein said device further comprises a plotter.

12. The method of claim 1, wherein said fluorescence is measured at an excitation wavelength in the range 490–550 nm and an emission wavelength in the range 570–610 nm.

13. The device of claim 5, wherein the fluorometer measures at an excitation wavelength in the range 490–550 nm and an emission wavelength in the range 570–610 nm.

14. The method of claim 2 wherein said microtiter plates have 96 measuring points.

15. The method of claim 1 wherein the cells are adherent.

\* \* \* \* \*

UNITED STATES PATENT AND TRADEMARK OFFICE
CERTIFICATE OF CORRECTION

PATENT NO. : 6,210,893 B1
DATED : April 3, 2001
INVENTOR(S) : Alexander Bürkle

It is certified that error appears in the above-identified patent and that said Letters Patent is hereby corrected as shown below:

<u>Title page,</u>
Item [73] should read: -- Deutsches Krebsforschungszentrum Stiftung Des Öffentlichen Rechts., Im Neuenheimer Feld 280, D-69120 Heidelberg, Germany --

Signed and Sealed this

Second Day of April, 2002

Attest:

Attesting Officer

JAMES E. ROGAN
Director of the United States Patent and Trademark Office